United States Patent [19]

Lund et al.

[11] Patent Number: 4,621,100

[45] Date of Patent: Nov. 4, 1986

[54] TREATMENT OF OSTEOPOROSIS WITH PROSTAGLANDINS

[75] Inventors: John E. Lund, Portage; Wanda B. High, Kalamazoo, both of Mich.

[73] Assignee: The Upjohn Company, Kalamazoo, Mich.

[21] Appl. No.: 659,138

[22] Filed: Oct. 9, 1984

Related U.S. Application Data

[63] Continuation of Ser. No. 353,549, Mar. 8, 1982, abandoned, and a continuation-in-part of Ser. No. 305,580, Sep. 25, 1981, abandoned, which is a continuation-in-part of Ser. No. 247,421, Mar. 25, 1981, abandoned.

[51] Int. Cl.$^4$ .................................... A61K 31/557
[52] U.S. Cl. .................................... 514/573; 514/155; 514/227; 514/249; 514/313; 514/315; 514/408; 514/530; 514/614; 514/693; 514/729
[58] Field of Search ............... 514/171, 573, 530, 155, 514/227, 249, 313, 315, 408, 614, 693, 729

[56] References Cited

U.S. PATENT DOCUMENTS

| | | | |
|---|---|---|---|
| 3,982,016 | 9/1976 | Walsh | 424/305 |
| 4,000,309 | 12/1976 | Walsh | 424/275 |
| 4,018,892 | 4/1977 | Walsh | 424/285 |
| 4,066,787 | 1/1978 | Okazaki et al. | 514/573 |
| 4,094,977 | 6/1978 | Seeger et al. | 514/171 |
| 4,097,601 | 6/1978 | Schaaf | 424/269 |
| 4,113,882 | 9/1978 | Okazaki et al. | 514/573 |
| 4,328,245 | 5/1982 | Yu et al. | 514/573 |
| 4,335,097 | 6/1982 | David et al. | 514/573 |

OTHER PUBLICATIONS

Frost–Bone Remodeling and Its Relationship to Metabolic Bone Diseases, (1973), Pub. Chas. Thomas, pp. 3–5, 36–41, 50–53, and 110.

D. Somjen, et al., Biochimica et Biophysica Acta, 627:91–100, (1980).

Yamasaki, et al., "Prostaglandin as a Mediator of Bone Resorption Induced by Experimental Tooth Movement in Rats", J. Dent. Res. 59(10):1635–1642 (10–80).

Tashjian, et al., "Biological Activities of Prostaglandin Analogs and Metabolites on Bone in Organ Culture", Nature, 266:645–647 (Apr. 1977).

Dietrich, et al., "Stimulation of Bone Resorption by Various Prostaglandins", Prostaglandins, vol. 10, No. 2, p. 631 (Aug. 1975).

Journal of Pediatrics 97:834–836 (1980).
Journal of Pediatrics 97:866–867 (1980).

Yonaga et al—Prostaglandins, vol. 17, (Apr.–Jun. 1979), pp. 801–804 and 813–819.

Primary Examiner—Sam Rosen
Attorney, Agent, or Firm—Lawrence T. Welch

[57] ABSTRACT

The present invention provides a novel method for treating osteoporoses, joint and dental diseases and increasing the rate of bone healing by orally administering certain prostaglandins. Further provided are novel compositions employing these prostaglandins.

7 Claims, No Drawings

TREATMENT OF OSTEOPOROSIS WITH PROSTAGLANDINS

CROSS REFERENCE TO RELATED APPLICATIONS

This application is a continuation of copending application Ser. No. 353,549, filed Mar. 8, 1982, now abandoned, which is a continuation-in-part of copending application Ser. No. 305,580, filed Sept. 25, 1981, now abandoned, and a continuation-in-part of application Ser. No. 247,421, filed Mar. 25, 1981, now abandoned.

BACKGROUND OF THE INVENTION

The present invention relates to novel methods of using known pharmacological agents. Particularly, the present invention relates to the use of certain prostaglandins in the treatment and prevention of bone diseases (particularly metabolic bone diseases, e.g., osteoporoses), and the treatment and prevention of joint and dental diseases in both humans and animals. This invention also relates to the use of these known pharmacological agents to increase the rate of bone healing in conditions of fractures, bone grafts and the like.

Medical research has found, in recent years, that most metabolic bone diseases (especially those in adults, e.g., osteoporosis proper) result from derangements of mechanisms governing the bone turnover processes (bone modeling and/or remodeling). These bone turnover processes contribute to the establishment of and subsequent maintainence of the mechanical competence of the skeleton. These processes operate by the coupled and coordinated activity of two continually renewing cell populations, and are initiated following some stimulus or "activation" that causes the proliferation and differentiation of these cells. These cells are osteoblasts and osteoclasts which have complimentary but directionally opposite activity. Osteoblasts are the cells which carry out the function of bone formation, and function in the healthy vertebrate together with osteoclasts, cells that function in the resorption and removal of bone.

The defective mechanisms of bone turnover leading to osteoporoses differ in the young and the adult. Growth and modeling are generally affected in the young, and remodeling (and modeling to some degree) are affected in the adult. Also, the young experience a defect in the expected accumulation of bone tissue, whereas an excessive loss of bone tissue is observed in the adult. Subnormal accumulation of bone tissue during growth, remaining asymptomatic during youth, can predispose an adult to develop osteoporosis or osteopenia.

The following definitions will be helpful in the understanding of this invention:

(a) "Osteopenia" is that skeletal condition of mammals characterized by a decreased volume of mineralized bone tissue.

(b) "Irreversible osteopenia" (osteoporosis) is that skeletal condition characterized by a reduction in total bone volume. (Distinguishing between total and mineralized bone volumes is thus important in the diagnosis of the disorder and its pathogenisis, and to assess the efficacy of treatment. See, e.g., Z. F. G. Jaworski, "Physiology and Pathology of Bone Remodeling," in Symposium on Osteoporosis in the Orthopedic Clinics of North America Vol. 12 (1981).)

(c) "Longitudinal Growth" refers to the enlargement of bone in length by the endochondral ossification process.

(d) "Appositional Growth" refers to that growth process which, when it acts alone (as observed in those skeletons following paralysis and diseases of congenital origin) causes uniform increases in all cross-sectional diameters and results in a basically circular diaphyseal cross section.

(e) "Modeling" refers to the process of bone activation followed by resorption at one bone site with a simultaneous activation of bone formation at another bone site. The modeling process accelerates certain diameters over others in response to biomechanical demands acting upon them. The modeling activity results in irregular cross sections with varying cortical thickness, as well as gross longitudinal curvatures of whole bone such as one finds normally in the clavicle, rib, radius, etc.

(f) "Remodeling" refers to the process of bone activation followed by resorption and then new bone formation at the same bone site in temporal sequence. The remodeling process results in modest changes in the relative amounts of bone resorbed and replaced on periosteal surfaces and causes a continued but slow expansion of the periosteal envelope throughout adult life.

Osteoporosis is a condition common in animals and particularly adult humans and typically results in a decrease in bone volume of both the bone matrix (the substrate, collagen), and the bone mineral, $Ca_{10}(PO_4)_6(OH)_2$ or "hydroxyapatite". Osteoporosis typically results in numerous symptomatic manifestations, including back pain, femoral neck fractures, Colles fractures, and deformation of the back bone. The bones of the afflicted animal may also become brittle, which increases the likelihood and incidences of fractures. Various types of osteoporosis are known. See for example The Merck Manual, 13th Edition, 1365–1366 (1977) and Dorland's Illustrated Medical Dictionary, 24th Edition. W. B. Saunders Company, London (1965).

Osteoporosis may be classified in many ways. One method of classification is by occurrence in life. Under this classification system, there exist osteoporoses of the following types:

1. Congenital, wherein the animal is born with a basic inability to accumulate bony tissue as rapidly and in the amounts necessary to meet the mechanical demands imposed on the skeleton. An example of this condition is called Osteogenesis Imperfecta.

2. Growth-related, wherein the animal during immaturity suffers from some condition which causes the growing skeleton to accumulate less bone than a normal growing skeleton and results in a individual with less than the normal amount of bone tissue. There is an alteration in bone formation, resorption, growth, modeling and remodeling processes. These osteoporoses are usually characterized by nearly normal periosteal diameters at midshaft relative to their lengths, but relatively enlarged marrow cavity and less than the normal steepness of metophyseal inflaring. Examples of this type of osteoporosis include biliary stenosis, eunuchism, arthrogryphosis (following paralysis due to poliomyelitis), muscular dystrophy, and certain osteoporoses which are secondary to a pre-existing hematopoietic disease, which conditions pathogenically resemble those of acquired osteoporosis (discussed infra) but occur in an immature skeleton.

3. Acquired osteoporoses, both symptomatic and asymptomatic, may be classified into a number of types, whose etiology is not well understood. Examples of this type of osteoporosis include senile osteoporosis, post menopausal osteoporosis, Cushing's Osteoporosis, Mast Cell Disease, Thyrotoxicosis, Primary Hyperparathyroidisim, True Disuse Osteoporosis, Post Traumatic Osteodystrophy and Burned-out Acromegaly.

Another method of classifying osteoporoses is by the change in bone dynamics. Under this classification, there exist the following classifications:

1. Osteoporoses characterized by decreased bone turnover rate—this includes decreased activation, resorption, and formation rates. Examples of this type of osteoporosis include senile osteoporosis; post menopausal osteoporosis, Cushing's Osteoporosis; Muscular Dystrophy; True Disuse Osteoporosis; Burned-out Acromegaly; Chronic Renal failure; and estrogen therapy. The first five osteoporoses are not reversed naturally, and affect primarily the endosteal surfaces. Burned-out Acromegaly is also not reversed naturally and affects primarily the endosteal and periosteal surfaces. Classic renal failure is not reversed naturally and little is known about estrogen therapy. There is no known or proven cure for any of these osteoporoses, and data on estrogenic therapy is not complete.

2. Osteoporoses characterized by increased bone-turnover rate: examples of these kinds of osteoporoses include thyrotoxicosis (which is reversible via surgery and affects primarily periosteal, haversian, and endosteal surfaces; certain kinds of osteogenesis imperfecta, which is not reversed naturally and affects primarily periosteal and endosteal surfaces; and post traumatic osteodystrophy, which is naturally reversable and effects primarily the periosteal, haversian, and endosteal surfaces.

3. Normal or variable bone-turnover rate: examples of this condition include mass cell disease (and similar conditions including neoplasia); Eunuchism; and Primary Hyperparathyroidism. The first two conditions are not reversed naturally and affect primarily the endosteal surface. Primary Hyperparathyroidism affects primarily the periosteal, haversian, and endosteal surfaces. The reversability of these conditions varies.

The method of the present invention should be useful in treating the conditions of bone dynamics described under 1 and 3 above.

Factors which affect bone-turnover include:

1. Endocrine factors: mesenchymal cell activation and thus remodeling rates are consistently increased in acromegaly and Thyrotoxicosis while they are decreased in Cushing's disease and analogous syndromes involving anti-inflammatory steroid therapy; oophorectomy; menopause; and the like.

2. Vascular factors: regional large increases in bone remodeling follows local tissue injury and consistently and proportionally is associated with increased tissue perfusion by the blood. The local tissue injury may consist of a fracture, a burn to overlying skin, obvious injury to underlying deep tissue, a surgical procedure of bone or soft tissue, local infections, etc.

3. Neurological factors: a transient increase in regional remodeling regularly occurs following trauma to, infection of, or transection of major peripheral nerves supplying the region; individuals suffering from poliomyeditis have consistently symmetrically circular cortices due to the lack of significant modeling activity and functional innervation.

4. Age Factors: bone turnover proceeds at a greater rate and frequency in the young compared to the adult. In some adult skeletons bone turnover may be only trivial resulting in significant clinical disease.

5. Mechanical factors: mechanical loading apparently directly stimulates skeletal turnover by manipulating microenvironmental factors of bone surfaces e.g. space travel for prolonged periods associated with reduced gravitational forces, prolonged bed rest, and the like.

6. Interceptive, repairative, and/or corrective surgical procedures involving diseased, deformed, and/or transplanted mineralized tissue;

7. Primary and/or Secondary Nutritional Factors (e.g., primary biliary and alcoholic cirrhosis); and 8. Renal dialysis.

A primary goal of osteoporosis therapy is to increase bone tissue mass by increasing bone formation and/or decreasing bone resorption.

The prostaglandins used in the present invention are derivatives of prostanoic acid. A trivial system of nomenclature has been devised, which classifies the prostaglandins according to the substituents on the cyclopentane ring. See, N. A. Nelson, *Journal of Medicinal Chemistry*, 17:911 (1974). For a further discussion of the prostaglandins, see Bergstrom, et al., Pharmacol. Rev. 20:1 (1968), and references cited therein.

The term prostaglandin analog herein refers to those compounds structurally related to the prostaglandins (in that they exhibit a cyclopentane, or adjacently homologous cycloalkane, ring and a pair of side chains attached to adjacent carbon atoms of the ring) which retain characteristic biological properties of the prostaglandins. See Bergstöm, cited above. Various structural modifications of the prostaglandins are known to produce useful prostaglandin analogs. Many of these structural modifications are discussed in the U.S. patents set forth below.

PRIOR ART

Numerous antiosteoporotic agents, i.e., agents proposed for the treatment or prevention of osteoporosis, are known in the art. Such agents include anabolic steroids, various phosphorus-containing agents, vitamin D and related substances, estrogenic steroids, fluoride, parathyroid hormone (PTH), and calcitonin. Also, certain aromatic carboxylic acids have been described as useful antiosteoporotic agents. For a detailed review and discussion of such antiosteoporotic agents, see U.S. Pat. No. 4,125,621 or U.S. Pat. No. 4,101,668.

Also known are numerous prostaglandins and their analogs. Thus, $PGE_1$ is disclosed in U.S. Pat. No. 3,069,322 and $PGE_2$ is disclosed in U.S. Pat. No. 3,598,858. $PGE_2$ esters are disclosed in U.S. Pat. Nos. 3,795,697 and 3,691,216. 20-Isopropylidene compounds are disclosed in Japanese Kokai No. 77-97946. Other prostaglandin analogs are disclosed in U.S. Pat. Nos. 3,069,322; 3,598,858; 3,636,120; 3,639,463; 3,691,216; 3,706,789; 3,725,454; 3,726,909; 3,728,382; 3,759,978; 3,776,938; 3,776,939; 3,795,697; 3,804,879; 3,804,889; 3,804,890; 3,812,172; 3,812,179; 3,813,433; 3,836,578; 3,839,409; 3,849,487; 3,852,337; 3,855,270; 3,880,912; 3,888,916; 3,890,372; 3,894,062; 3,929,861; 3,929,862; 3,959,319; 3,962,293; 3,968,140; 3,969,376; 3,969,377; 3,969,380; 3,974,189; 3,974,195; 3,987,084; 3,998,867; 3,998,869; 4,005,133; 4,017,535; 4,032,576; 4,057,564; 4,060,534; 4,067,891; 4,069,386; 4,081,471; 4,082,783; 4,084,063; 4,098,805; 4,103,098; 4,119,666; 4,128,577; 4,130,584; 4,130,720; 4,130,721; 4,139,564; 4,158,667; 4,171,460; 4,176,236; 4,197,257; 4,205,178; 4,220,796;

3,903,131; 3,954,741; 4,187,381; 3,972,917; 4,052,512; 3,823,180; 4,107,191; 4,147,879; and 4,165,436.

The ability of certain prostaglandins to stimulate bone resorption in vitro is well known.

D. Somjen, et al., in Biochimica et Biophysica Acta, 627:91-100 (1980), states that $PGE_2$ and cyclic AMP production is increased when physical stress is placed on cultured bone cells in a petri dish.

Yonaga, et al., in Prostaglandins, 17:801 (June 1979) evaluated the effects of $PGE_1$ in a growth-related osteoporotic skeleton. From the data presented it cannot be determined what effect $PGE_1$ would have on nongrowth related osteoporosis. Growth related osteoporosis (e.g., muscular dystrophy, Still's Disease, congenital biliary stenosis and eunuchism) occurs during immaturity where some condition develops which causes the growing skeleton subsequently to accumulate less bone than a normal growing skeleton and results in an individual having less than the normal amount of bone tissue. See, Frost, H. M., *Bone Remodeling and Its Relationship to Metabolic Bone Diseases.* (Charles C. Thomas, Banner House, 1973).

Several other authors have written on the effects of PGE-type prostaglandins on bone growth. See, e.g., Yamasaki, et al., "Prostaglandin as a Mediator of Bone Resorption Induced by Experimental Tooth Movement in Rats," J. Dent. Res. 59 (10):1635-1642 (October 1980); Tashjian, et al., "Biological Activities of Prostaglandin Analogs and Metabolites on Bone in Organ Culture," Nature, 266:645-647 (April 1977); and Dietrich, et al., "Stimulation of Bone Resorption by Various Prostaglandins," Prostaglandins, Vol. 10, No. 2, p. 631 (August 1975). The first reference discloses that $PGE_1$ and $PGE_2$ increase bone resorption in rats. The latter two references also disclose that prostaglandins are mediators of bone resorption. Further, the latter experiments were conducted in in vitro systems, which cannot adequately predict a drug's therapeutic value when it comes to the treatment of osteoporosis in a dynamic, complex, living system such as that present in individuals suffering from most nongrowth related osteoporotic diseases which are treated by the method of the present invention.

Two recent articles in the Journal of Pediatrics, 97:834-836 and 97:866-867 (1980) describe proliferative bone changes in infants following long term infusion of $PGE_1$.

U.S. Pat. No. 3,982,016, and U.S. Pat. Nos. 4,000,309 and 4,018,892, divisions thereof, disclose that certain 13,14-dihydro-$PGE_2$ p-biphenyl esters are useful for increasing bone deposition in the treatment of osteopenia. U.S. Pat. No. 4,097,601 discloses that certain 2-descarboxy-2-(tetrazol-5-yl)-11-desoxy-16-aryl-prostaglandins are useful for increasing bone deposition in certain bone disorders. This latter patent notes that the effect of this class of synthetic prostaglandins is unexpected in view of the fact that the natural prostaglandins are known to increase bone resorption.

SUMMARY OF THE INVENTION

Surprisingly and unexpectedly it has been found that a broad class of prostaglandins, both natural and synthetic, are useful in increasing bone deposition and treating bone disorders.

Thus, the present invention provides (1) a method for the treatment or prevention of nongrowth related osteoporosis in an animal suffering from or susceptible to osteoporosis which comprises systemically administering to said animal an amount of a compound of the Formula I

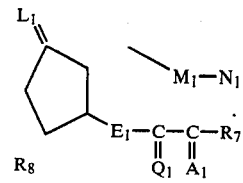

wherein $N_1$ is
(1) $-COOR_1$, wherein $R_1$ is
  (a) hydrogen,
  (b) $(C_1-C_{12})$alkyl
  (c) $(C_1-C_{10})$cycloalkyl,
  (d) $(C_6-C_{12})$aralkyl,
  (e) phenyl, optionally substituted with one, 2 or 3 chloro or $(C_1-C_3)$alkyl,
  (f) phenyl substituted in the para position by
    (i) $-NH-CO-R_{25}$,
    (ii) $-CO-R_{26}$,
    (iii) $-O-CO-R_{54}$, or
    (iv) $-CH=N-NH-CO-NH_2$ wherein $R_{25}$ is methyl, phenyl, acetamidophenyl, benzamidophenyl, or $-NH_2$; $R_{26}$ is methyl, phenyl, $-NH_2$, or methoxy; and $R_{54}$ is phenyl or acetamidophenyl; inclusive, or
  (g) a pharmacologically acceptable cation;
(2) $-CH_2OH$,
(3) $-COL_4$, wherein $L_4$ is
  (a) amino of the formula $-NR_{51}R_{52}$, wherein $R_{51}$ and $R_{52}$ are
    (i) hydrogen
    (ii) $(C_1-C_{12})$alkyl,
    (iii) $(C_3-C_{10})$cycloalkyl,
    (iv) $(C_7-C_{12})$aralkyl,
    (v) phenyl, optionally substituted with one, 2 or 3 chloro, $(C_1-C_3)$alkyl, hydroxy, carboxy, $(C_2-C_5)$alkoxycarbonyl, or nitro,
    (vi) $(C_2-C_5)$carboxyalkyl,
    (vii) $(C_2-C_5)$carbamoylalkyl,
    (viii) $(C_2-C_5)$cyanoalkyl,
    (ix) $(C_3-C_6)$acetylalkyl,
    (x) $(C_7-C_{11})$benzoalkyl, optionally substituted by one, 2 or 3 chloro, $(C_1-C_3)$alkyl, hydroxy, $(C_1-C_3)$alkoxy, carboxy, $(C_2-C_5)$alkoxycarbonyl, or nitro,
    (xi) pyridyl, optionally substituted by one, 2 or 3 chloro, $(C_1-C_3)$alkyl, or $(C_1-C_3)$alkoxy,
    (xii) $(C_6-C_9)$pyridylalkyl optionally substituted by one, 2 or 3 chloro, $(C_1-C_3)$alkyl,
    (xiii) $(C_1-C_4)$hydroxyalkyl,
    (xiv) $(C_1-C_4)$dihydroxyalkyl,
    (xv) $(C_1-C_4)$trihydroxyalkyl,
  with the further proviso that not more than one of $R_{51}$ and $R_{52}$ is other than hydrogen or alkyl,
  (b) cycloamino selected from the group consisting of pyrolidino, piperidino, morpholino, piperazino, hexamethyleneimino, pyrrolino, or 3,4-didehydropiperidinyl optionally substituted by one or 2 $(C_1-C_{12})$alkyl of one to 12 carbon atoms, inclusive,
  (c) carbonylamino of the formula $-NR_{53}COR_{51}$, wherein $R_{53}$ is hydrogen or $(C_1-C_4)$alkyl and $R_{51}$ is other than hydrogen, but otherwise as defined above,
  (d) sulfonylamino of the formula $-NR_{53}SO_2R_{51}$, wherein $R_{51}$ and $R_{53}$ are as defined in (c), (e) —$CH_2NL_2L_3$, wherein $L_2$ and $L_3$ are hydrogen or ($C_1$-$C_4$)alkyl, being the same or different, or the pharmacologically acceptable acid addition salts thereof when $N_1$ is —$CH_2NL_2L_3$, (f) —$CO_2R_1$, (g) —$CH_2OH$, (h) —$CONR_5R_6$, (i) —$CH_2$—$NR_5R_6$, or (j) —$CONHSO_2CH_3$;

wherein $M_1$ is cis or trans—CH=CH—$(CH_2)_m$—, —$(CH_2)_n$—, —$(CH_2)_{n-1}$—$CF_2$—, —CO—$(CH_2)_3$—$CH_2$—, trans—$(CH_2)_m$—CH=CH—; —CH=CH—$(CH_2)_{m-1}$—$CF_2$—, or —CO—$(CH_2)_3$—$CF_2$—;

wherein $L_1$ is α—OH:β—H, =$CH_2$, or oxo;

wherein $R_8$ is hydrogen, hydroxy, or methyl;

wherein $E_1$ is trans—CH=CH, —$CH_2$—$CH_2$—, or —C≡C—;

wherein $Q_1$ is α—OH:β—$R_2$, α—$R_2$:β—OH, or oxo;

wherein $A_1$ is α—H:β—$CH_3$, α—$CH_3$:β—H; α—H:-β—H, α—F:β—F or α—$CH_3$:β—$CH_3$;

wherein $R_7$ is:

(1) —$(CH_2)_p$—$CH_3$, (2) cis—CH=CH—$CH_2$—$CH_3$, (3) —$(CH_2)_2$—C≡CH, (4) —$(CH_2)_3$—CH=C$(CH_3)_2$, or (5) —C($R_3R_4$)—$(CH_2)_g$—$CH_2R_{14}$;

wherein $R_2$ is hydrogen or methyl;

wherein $R_3$ and $R_4$ are the same or different and are hydrogen or methyl;

wherein $R_5$ and $R_6$ are the same or different and are hydrogen, methyl, or ethyl;

wherein $R_{14}$ is hydrogen or ($C_1$-$C_4$)alkyl;

wherein g is an integer of from one to 4, inclusive;

wherein m is an integer of from 3 to 5, inclusive;

wherein n is an integer of from 5 to 7, inclusive; and wherein p is an integer of from one to 6, inclusive; or the pharmacologically acceptable salts thereof when $N_1$ is —$CONR_{53}SO_2R_{51}$; in an amount effective to treat or prevent said osteoporosis;

(2) in a method of preventing or treating osteoporosis with one or more known antiosteoporotic agents selected from the group consisting of anabolic steroids, estrogenic steriods, vitamin D and its metabolites, phosphorous-containing agents, PTH, inorganic fluoride-containing agents, calcium salts, and calcitonin, the improvement which comprises:

concomittantly administering an amount of a compound of the Formula I wherein all variables are as defined as above, which, together with said known antiosteoporotic agent or agents, is effective to treat or prevent said osteoporosis;

(3) in a unit dose of a pharmaceutical composition for preventing or treating osteoporosis with one or more known antiosteoporotic agents selected from the group consisting of anabolic steroids, estrogenic steroids, vitamin D and its metabolites, phosphorus-containing agents, PTH, inorganic fluoride-containing agents, calcium salts, and calcitonin, the improvement which comprises:

an amount of a compound of the Formula I wherein all variables are defined as above, which, together with said known antiosteoporotic agent or agents, is an effective unit dose to treat or prevent said osteoporosis;

(4) a method for increasing the bone fracture healing rate in an animal exhibiting a bone fracture which comprises:

systemically administering to said animal an amount of a prostaglandin of the Formula I, wherein all variables are defined as above, effective to increase said bone fracture healing rate;

(5) a method for enhancing the success rate of bone grafts which comprises: systemically administering to an animal in need of such a bone graft an amount of a compound of the Formula I, wherein all variables are defined as above, effective to increase said success rate; and (6) a method to enhance the reconstruction and/or healing of alveolar sockets in relation to teeth in an animal suffering from dental disease which comprises: systemically administering to said animal an amount of a compound of the Formula I, wherein all variables are defined as above, effective to enhance said reconstruction and/or healing.

In accomplishing the purposes of this invention those compounds which are useful are those prostaglandins and prostaglandin derivatives of the Formula I described above. These compounds significantly increase bone mass and enhance bone turnover in the dog under conditions similar to those described in Example 1. Prostaglandins which are at least 1% as potent as $PGE_2$ under these conditions significantly increase bone mass and enhance bone turnover. The term "antiosteoporotic $PGE_2$-type prostaglandins" is meant to include all such prostaglandins and related compounds. Examples of such compounds include:

$PGE_1$;

2-decarboxy-2-hydroxymethyl-$PGE_1$;

$PGE_2$;

15-keto-$PGE_2$;

16,16-dimethyl-$PGE_2$;

17S,20-dimethyl-6-oxo-$PGE_1$, methyl ester;

17S,20-dimethyl-trans-delta-2-$PGE_1$;

$PGE_2$, N-methanesulfonylamide;

9-deoxo-9-methylene-16,16-dimethyl-$PGE_2$;

(15S)-15-methyl-$PGE_2$;

(15R)-15-methyl-$PGE_2$;

11-deoxy-16,16-dimethyl-$PGE_2$;

11-deoxy-11α-16,16-trimethyl-$PGE_2$;

6-oxo-11-deoxy-11α,16,16-trimethyl-$PGE_2$;

6-oxo-$PGE_2$;

6-oxo-$PGE_1$;

2-decarboxy-2-hydroxymethyl-$PGE_1$;

11-deoxy-15-methyl-$PGE_1$;

$PGE_3$;

16,16-difluoro-$PGE_2$; and 20-isopropylidene-$PGE_1$ as well as the alkyl esters, pharmacologically acceptable salts and derivatives thereof.

$PGE_2$ is the most preferred compound of this invention.

Also preferred are: 15-keto-$PGE_2$-type compounds, particularly 15-keto-$PGE_2$; and the stable esters of 16,16-dimethyl-$PGE_2$, particularly the p-(p-acetamidobenzamide) phenyl ester and the α-semicarbazonon-p-tolyl ester.

With regard to the divalent substituents described above (e.g., $L_1$, $Q_1$ and $A_1$), these divalent radicals are defined as α-$R_i$:β-$R_j$, wherein $R_i$ represents the substituent of the divalent moiety in the alpha configuration with respect to the plane of the C-8 to C-12 cyclopentane ring and $R_j$ represents the substituent of the divalent moiety in the beta configuration with respect to the plane of the ring. Accordingly, when $L_1$ is defined as α—OH:β—H, the hydroxy of the $L_1$ moiety is in the alpha configuration and the hydrogen substituent is in the beta configuration.

The carbon atom content of various hydrocarbon-containing moieties is indicated by a prefix designating the minimum and maxiumum number of carbon aoms in the moiety, i.e., the prefix ($C_i$-$C_j$) indicates a moiety of the integer "i" to the integer "j" carbon atoms, inclusive. Thus ($C_1$-$C_3$)alkyl refers to alkyl of one to 3 carbon atoms, inclusive, or methyl, ethyl, propyl, and isopropyl.

When $Q_1$ contains a methyl substituent the compounds are all named as "15-methyl" compounds. Further, when the $E_1$ moiety contains an hydroxyl in the beta configuration are additionaly named as "15-epi" compounds. The prostaglandin compounds herein which contain —$(CH_2)_2$—, or —C≡C— as the $E_1$ moiety, are accordingly referred to as "13,14-dihydro", or "13,14-didehydro" compounds, respectively.

When $R_7$ is straight chained —$(CH_2)_pCH_3$ wherein m is as defined above, the compounds so described are named as "19,20-dinor", "20-nor", "20-methyl" or "20-ethyl" compounds when p is one, 2, 4, or 5, respectively. When $R_7$ is branched chain —$C(R_3R_4)$—$(CH_2)_g$—$CH_2R_{14}$, then the compounds so described are "17-, 18-, 19-, or 20-alkyl" or "17,17-, 17,18-, 17,19-, 17,20-, 18,18-, 18,19-, 18,20-, 19,19-, or 19,20-dialkyl" compounds when g is 4 or 5 and the unbranched portion of the chain is at least n-butyl, e.g., "17,20-dimethyl" compounds are descibed when g is 5 (1-methylpentyl).

When $R_7$ is cis—CH═CH—$CH_2CH_3$, the compounds so described are named as "cis-17,18-didehydro" compounds.

When $R_7$ is —$(CH_2)_3$—CH═$C(CH_3)_2$, the compounds so described are named as "20-isopropylidene" compounds.

When $N_1$ is —$COL_4$, the compounds herein are named as amides. Further, when $N_1$ is —$COOR_1$, the compounds herein are named as prostaglandin esters and salts.

Examples of novel amides herein (i.e., $N_1$ is —$COL_4$) include the following:

(1) Amides within the scope of alkylamino groups of the formula $NR_{51}R_{52}$ are methylamide, ethylamide, n-propylamide, n-butylamide, n-pentylamide, n-hexylamide, n-heptylamide, n-octylamide, n-nonylamide, n-decylamide, n-undecylamide, and n-dodecylamide, and isomeric forms thereof. Further examples are dimethylamide, diethylamide, di-n-propylamide, di-n-butylamide, methylethylamide, methylpropylamide, methylbutylamide, ethylpropylamide, ethylbutylamide, and propylbutylamide. Amides within the scope of cycloalkylamino are cyclopropylamide, cyclobutylamide, cyclopentylamide, 2,3-dimethylcyclopentylamide, 2,2-dimethylcyclopentylamide, 2-methylcyclopentylamide, 3-tert-butylcyclopentyl amide, cyclohexylamide, 4-tert-butylcyclohexylamide, 3-isopropylcyclohexylamide, 2,2-dimethylcyclohexylamide, cycloheptylamide, cyclooctylamide, cyclononylamide, cyclodecylamide, N-methyl-N-cyclobutylamide, N-methyl-N-cyclopentylamide, N-methyl-N-cyclohexylamide, N-ethyl-N-cyclopentylamide, and N-ethyl-Ncyclohexylamide. Amides within the scope of aralkylamino are benzylamide, 2-phenylethylamide, and N-methyl-N benzylamide. Amides within the scope of substituted phenylamide are p-chloroanilide, m-chloroanilide, 2,4-dichloroanilide, 2,4,6-trichloroanilide, m-nitroanilide, p-nitroanilide, p-methoxyanilide, 3,4-dimethoxyanilide, 3,4,5-trimethoxyanilide, p-hydroxymethylanilide, p-methylanilide, m-methyl anilide, p-ethylanilide, t-butylanilide, p-carboxyanilide, p-methoxycarbonyl anilide, p-carboxyanilide and o-hydroxyanilide. Amides within the scope of carboxyalkylamino are carboxyethylamide, carboxypropylamide and carboxymethylamide, carboxybutylamide. Amides within the scope of carbamoylalkylamino are carbamoylmethylamide, carbamoylethylamide, carbamoylpropylamide, and carbamoylbutylamide. Amides within the scope of cyanoalkylamino are cyanomethylamide, cyanoethylamide, cyanopropylamide, and cyanobutylamide. Amides within the scope of acetylalkylamino are acetylmethylamide, acetylethylamide, acetylpropylamide, and acetylbutylamide. Amides within the scope of benzoylalkylamino are benzoylmethylamide, benzoylethylamide, benzoylpropylamide, and benzoylbutylamide. Amides within the scope of substituted benzoylalkylamino are p-chlorobenzoylmethylamide, m-chlorobenzoylmethylamide, 2,4-dichlorobenzoylmethylamide, 2,4,6-trichlorobenzoylmethylamide, m-nitrobenzoylmethylamide, p-nitrobenzoylmethylamide, p-methoxybenzoylmethylamide, 2,4-dimethoxy benzoylmethylamide, 3,4,5-trimethoxybenzoylmethylamide, p-hydroxymethylbenzoylmethylamide, p-methylbenzoylmethylamide, m-methylbenzoylmethylamide, p-ethylbenzoylmethylamide, t-butylbenzoylmethylamide, p-carboxybenzoylmethylamide, m-methoxycarbonylbenzoylmethylamide, o-carboxybenzoylmethylamide, o-hydroxybenzoylmethylamide, p-chlorobenzoylethylamide, m-chlorobenzoylethylamide, 2,4-dichlorobenzoylethylamide, 2,4,6-trichlorobenzoylethylamide, m-nitrobenzoylethylamide, p-nitrobenzoylethylamide, p-methoxybenzoylethylamide, p-methoxybenzoylethylamide, 2,4-dimethoxybenzoylethylamide, 3,4,5trimethoxybenzoylethylamide, p-hydroxymethylbenzoylethylamide, p-methylbenzoylethylamide, m-methylbenzoylethylamide, p-ethylbenzoylethylamide, t-butylbenzoylethylamide, p-carboxybenzoylethylamide, m-methoxycarbonylbenzoylethylamide, o-carboxybenzoylethylamide, o-hydroxybenzoylethylamide, p-chlorobenzoylpropylamide, m-chlorobenzoylpropylamide, 2,4-dichlorobenzoylpropylamide, 2,4,6-trichlorobenzoylpropylamide, m-nitrobenzoylpropylamide, p-nitrobenzoylpropylamide, p-methoxybenzoylpropylamide, 2,4-dimethoxybenzoylpropylamide, 3,4,5-trimethoxybenzoylpropylamide, p-hydroxymethylbenzoylpropylamide, p-methylbenzoylpropylamide, m-methylbenzoylpropylamide, p-ethylbenzoylpropylamide, t-butylbenzoylpropylamide, p-carboxybenzoylpropylamide, m-methoxycarbonylbenzoylpropylamide, o-carboxybenzoylpropylamide, o-hydroxybenzoylpropylamide, p-chlorobenzoylbutylamide, m-chlorobenzoylbutylamide, 2,4-dichlorobenzoylbutylamide, 2,4,6-trichlorobenzoylbutylamide, m-nitrobenzoylbutylamide, p-nitrobenzoylbutylamide, p-methoxybenzoylbutylamide, 2,4-dimethoxybenzoylbutyl-amide, 3,4,5-trimethoxybenzoylbutylamide, p-hydroxymethylbenzoylbutyl-amide, p-methylbenzoylbutyamide, m-methylbenzoylbutylamide, p-ethyl-benzoylbutyalmide, m-methylbenzoylbutylamide, p-ethylbenzoylbutyl-amide, t-butylbenzoylbutylamide, p-carboxybenzoylbutylamide, m-methoxycarbonylbenzoylbutylamide, o-carboxybenzoylbutylamide, o-hydroxybenzoylmethylamide. Amides within the scope of pyridylamino are α-pyridylamide, β-pyridylamide, and γ-pyridylamide. Amides within the scope of substituted pyridylamino are 4-methyl-α-pyridylamide, 4-methyl- β-pyridylamide, 4-chloro-α-pyridylamide, and 4-chloro-β-pyridylamide. Amides within the scope of pyridylalkylamino are α-pyridylmethylamide, β-pyridylmethylamide, β-pyridylmethylamide, α-pyridylethylamide, β-pyridylethylamide, γ-pyridylethylamide, α-pyridylpropylamide, β-pyridylpropylamide, γ-pyridylpropylamide, α-pyridylbutylamide, β-pyridylbutylamide, and γ-pyridylbutylamide. Amides within the scope of substituted pyridylalkylamido are 4-methyl-α-pyridylmethylamide, 4-methyl-β-pyridylmethylamide, 4-chloro-α-pyridylmethylamide, 4-chloro-β-pyridylmethylamide, 4-methyl-α-pyridylpropylamide, 4-methyl-β-pyridylpropylamide, 4-chloro-α-pyridylpropylamide, 4-chloro-β-pyridylpropylamide, 4-methyl-α-pyridylbutylamide, 4-methyl-β-pyridylbutylamide, 4-chloro-α-pyridylbutylamide, 4-chloro-β-pyridylbutylamide, 4-chloro-γ-pyridylbutyl-amide. Amides within the scope of hydroxyalkylamino are hydroxymethylamide, β-hydroxyethylamide, β-hydroxypropylamide, γ-hydroxypropylamide, 1-(hydroxymethyl)ethyl-amide, 1-(hydroxymethyl)propylamide, (2-hydroxymethyl)propylamide, and α,α,-dimethyl-hydroxyethylamide. Amides within the scope of dihydroxyalkylamino are dihydroxymethylamide, β,γ-dihydroxypropylamide, 1-(hydroxymethyl)2-hydroxymethylamide, β,γ-dihydroxybutylamide, β,δ-dihydroxybutyl-amide, γ,δ-dihydroxybutylamide, and 1,1-bis(hydroxymethyl)ethylamide. Amides within the scope of trihydroxyalkylamino are tris(hydroxymethyl)-methylamide and 1,3-dihydroxy-2-hydroxymethylpropylamide.

(2) Amides within the scope of the cycloamino groups described above are pyrrolidylamide, piperidylamide, morpholinylamide, hexamethyleneiminylamide, piperazinylamide, pyrrolinylamide, and 3,4-didehydropiperidinylamide.

(3) Amides within the scope of carbonylamino of the formula —NR$_{53}$COR$_{51}$ are methylcarbonylamide, ethylcarbonylamide, phenylcarbonylamide, and benzylcarbonylamide.

(4) Amides within the scope of sulfonylamino of the formula —NR$_{53}$SO$_2$R$_{51}$ are methylsulfonylamide, ethylsufonylamide, phenylsulfonylamide, p-tolylsulfonylamide, benzylsulfonylamide.

Examples of alkyl of one to 12 carbon atoms, inclusive, are methyl, ethyl, propyl, butyl, pentyl, hexyl, heptyl, octyl, nonyl, decyl, undecyl, dodecyl, isomeric forms thereof.

Examples of ($C_3$–$C_{10}$)cycloalkyl which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl.

Examples of ($C_7$–$C_{12}$)aralkyl are benzyl, 2-phenylethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 4 carbon atoms, inclsive, are p-chlorophenyl, m-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2-methylphenyl, and 2,4-dichloro-3-methylphenyl.

Examples of ($C_5$–$C_7$)cycloalkyl optionally substituted by ($C_1$–$C_4$)-alkyl are cyclobutyl, 1-propylcyclobutyl, 1-butylcyclobutyl, 1-pentylcyclobutyl, 2-methylcyclobutyl, 2-propylcyclobutyl, 3-ethylcyclobutyl, 3-propylcyclobutyl, 2,3,4-triethylcyclobutyl, cyclopentyl, 2,2-dimethylcyclopentyl, 3-ethylcyclopentyl, 3-propylcyclopentyl, 3-butylcyclopentyl, 3-tert-butylcyclopentyl, 1-methyl-3-propylcyclopentyl, 2-methyl-3-propylcyclopentyl, 2-methyl-4-propylcyclopentyl, cyclohexyl, 3-ethylcyclohexyl, 3-isopropylcyclohexyl, 4-methylcyclohexyl, 4-ethylcyclohexyl, 4-propylcyclohexyl, 4-butylcyclohexyl, 4-tert-butylcyclohexyl, 2,6-dimethylcyclohexyl, 2,2-dimethylcyclohexyl, 2,6-dimethyl-4-propylcyclohexyl, and cycloheptyl.

Pharmacologically acceptable cations within the scope of $R_1$ include the pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the like aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)-diethanolamine, glactamine, N-methylglycamine, N-methylglucosamine, ephedrine, phenylephrine, epinephrine, procaine, and the like. Further useful amine salts are the basic amino acid salts, e.g., lysine and arginine.

Examples of suitable pharmacologically acceptable quaternary ammonium cations are tetramethylammonium, tetraethylammonium, benzyltrimethylammonium, phenyltriethylammonium, and the like.

The prostaglandins within the scope of this invention are known and can be synthesized by the methods described in the U.S. patents noted in the prior art statement above.

The present invention relates to the treatment of animals, although mammals and domesticated fowls represent particularly preferred embodiments of the present invention. Most preferred is the treatment of humans by the instant method. The present invention thus provides a method of treating both humans and valuable domestic animals, such as bovine, equine, canine, and feline species, and chickens, turkeys, geese, and other fowl.

In the prophylactic use of these antiosteoporotic prostaglandins, the dose effective for the prevention of the osteoporosis is determined by patient or animal response, as discussed hereinafter for therapeutic uses, and is, in general, somewhat less than the dose required to treat osteoporosis.

The employment of sound medical therapy requires that the antiosteoporotic prostaglandin be employed prophylactically only in cases where the animal or patient is particularly susceptible to the development of osteoporosis. These conditions and circumstances which increase susceptibility to osteoporosis described above are readily ascertainable to the ordinarily skilled physician or veterinarian.

Osteoporosis which is arrested or prevented in accordance with the present invention includes each of the various states or conditions described above where the long-term effects on the animal are untoward, and hence the condition or state is associated with a direct or indirect pathological process.

The method of the present invention is employed to increase the rate of bone fracture healing. Bone fractures may be the result of osteoporotic conditions as described above, or they may result from physical injuries incurred by otherwise healthy individuals in the course of everyday life (e.g., sports injuries, slip and fall injuries, auto accidents, and the like). The method of the present invention is thus useful in the treatment of bone fractures, however incurred.

The utility and rationale of the proposed treatment for fractures, including delayed-unions also applies to its utility regarding reconstructive surgical procedures: e.g., bone grafts and dental procedures. Low bone turnover and inadequate skeletal response to biomechanical stimuli result in inadequate quality and quantity of bone and delayed repair of microdamage. In these individuals the mechanisms responsible for bone repair (preventing the accumulation of microdamage in normal healthy individuals) are less responsive to stimuli that normally induce bone healing. Similarly the lack of sufficient response of the skeleton of these individuals to reconstructive procedures (including dental and bone grafts, particularly those of the spine) result in delayed healing. An agent that can increase the stimulus of bone repair (increasing the activation of bone turnover and cells responsible for repair) results in sufficient skeletal response to decrease the time required for skeletal healing.

All of the above are not uncommon conditions encountered in medical or veterinary practice. Accordingly, the diagnosis of such conditions is readily undertaken by the ordinarily skilled physician or veterinarian.

While any convenient route of administration may be employed, oral formulation and oral administration are preferred. The choice of the route of administration is readily undertaken by an ordinarily skilled veterinarian or physician.

The dosage regimen for the prostaglandin employed is selected in accordance with a variety of factors, including the type, age, weight, sex, and medical condition of the mammal, the severity of osteoporosis and its duration, and the particular antiosteoporotic prostaglandin being administered. An ordinarily skilled physician or veterinarian, subsequent to the diagnosis of osteoporosis or bone fracture will readily determine and prescribe the effective amount of the antiosteoporotic prostaglandin to treat the condition. In so proceeding, the physician or veterinarian would, in treating osteoporosis for example, employ relatively low dosages of the compound, subsequently increasing the dose until a maximum response was obtained. Such a response is obtained when the total bone mass ceases to diminish or begins to increase.

Thus, the physician or veterinarian would by one method start at a relatively low dose of the antiosteoporotic prostaglandin. For example, for oral administration of $PGE_2$ he would start with about 0.1 mg/kg/day to about 0.2 mg/kg/day, and observe the response of the human or animal patient for several weeks. The dose of the prostaglandin is then adjusted downward or upward until the optimum effective dose is found. For example, the maximum needed dose will usually not exceed 10 mg/kg/day, although it may be necessary to occasionally exceed these doses when the osteoporosis is especially severe. Once the minimum effective dose of the particular prostaglandin is determined for a particular subject, it is advantageous to provide the subject with the dosage schedule which will provide a substantially uniform level of antiosteoporotic prostaglandin to the system. Thus, it is preferred to employ 0.1 to 0.4 mg/kg/day of the antiosteoporotic prostaglandin in the method of this invention when oral administration is used. 0.1 to 0.2 mg/kg/day is most preferred. Equivalent dosages for other routes of administration are also employed. An equivalent dose range is employed for the other antiosteoporotic prostaglandins based on their potency in relation to $PGE_2$ in the test system described in Example 2.

The employment of sound medical therapy requires that the prostaglandin be employed prophylactically only in the cases where the animal or patient is particularly susceptible to the development of osteoporosis. The conditions and circumstances which increase the susceptibility to osteoporosis are readily ascertainable to the ordinary skilled physician or veterinarian and include the factors set out above.

The use of the antiosteoporotic prostaglandins is, by a further embodiment of the present invention, undertaken concomitantly with other forms of conventional therapy for osteoporosis. Such other forms of conventional therapy include, for example, the various chemical therapies described in U.S. Pat. No. 4,125,612. When such combination therapies are employed, significant antiosteoporotic effects are often obtained with reduced effective dosages of the compounds employed herein.

In accordance with this further embodiment of the present invention, there are provided novel pharmaceutical compositions for antiosteoporotic therapy. These novel compositions consist of combinations of two or more active agents, one such agent being an antiosteoporotic prostaglandin and the second and further agents being the heretofore known agents for the treatment for osteoporosis and osteoporotic conditions. Such previously known antiosteoporotic agents include anabolic steroids, estrogenic steroids, calcium salts, inorganic fluoride, and calcitonin from various sources. Such novel compositions are advantageously used in arresting osteoporosis, often permitting a reduced dosage of the instant antiosteoporotic prostaglandin than that which would be required were it the sole therapy for treating or preventing osteoporosis.

In these novel pharmaceutical compositions, the instant prostaglandins are employed for each unit dosage is an amount equal to the amount of the compound were it the sole therapy down to not less than 50% thereof. The other conventional antiosteoporotic agent or agents are present therein at the known amounts employed in the treatment of osteoporosis.

The method of the present invention is an improvement over existing methods of osteoporotic treatment. Most currently used methods of treatment merely attempt to slow the rate of bone loss in osteoporosis. The method of the present invention actually increases the amount of total bone mass and turnover present and thus represents an advance in the art.

Surprisingly and unexpectedly oral administration of $PGE_2$-type compounds as in Example 2 is more convenient, more controlled and produces a better kind of bone than the intravenous use of $PGE_1$ as disclosed in Example 1. Thus, while the administration of both $PGE_1$ and $PGE_2$ resulted in an increase in bone turnover (affecting all bone surfaces), and in periosteal hyperostosis in a dose-related pattern, the $PGE_2$ bone effects were after oral administration for 90 days rather than intravenous administration for 30 days as with $PGE_1$. An orally administrated drug will obviously better facilitate therapeutic use. Also, the subperiosteal new bone obtained with $PGE_2$ was laminar in character (consisting largely of fibrous and lamellar bone interspersed with primary osteons) compared to the subperiosteal new woven bone obtained with $PGE_1$. In addition, the increase in remodeling activity after $PGE_1$ administration was tremendous, resulting in some cortical porosity, whereas $PGE_2$ increased remodeling foci and activity without producing obvious porous bone. Comparatively $PGE_2$ is a potent activator of bone remodeling and new bone formation without obvious deleterious effects compared to $PGE_1$ (at least by the dosages and routes used), with the potential for permitting better control on bone-induced effects. Also, the new bone that was laminar in character after $PGE_2$ administration is better capable of meeting biomechanical demands of the skeleton than woven bone.

This is the first demonstration of an agent that can selectively induce laminar bone de novo, in vivo, without artificial implantations or obvious foreign (exogenous) components. This invention thus provides for the therapeutic use of a basically endogenous (vs. exogenous, foreign) agent in the treatment of bone and related diseases alone and in combination with other agents or procedures. Thus, this invention provides a potent activator of bone turnover, allowing potentially selective regulation and alteration of bone dynamics, bone cell function and the microenvironment of bone cells, affecting both the quality and quantity of bone.

The present invention thus provides a surprising and unexpected method of use for a class of pharmacological agents previously known to be useful for unrelated pharmaceutical purposes.

DESCRIPTION OF THE PREFERRED EMBODIMENTS

The efficacy of the prostaglandins and related compositions in treating osteoporosis and increasing the rate of bone fracture healing is seen by the example given below.

EXAMPLE 1

The effects of $PGE_1$ on the deposition of bone in animals was tested in the following manner: four groups of beagle dogs, age 9-15 months, were administered various concentrations of $PGE_1$ or control by continuous intravenous infusion. Each group of dogs contained two male and two female animals. The first three groups were administered 25, 80, and 250 ng/kg/minute of $PGE_1$, respectively. The fourth group received the diluent alone, which was comprised of 10% ethanol in 0.05 molar tris buffer, having a pH of 7.1. The animals approximate body weight range at the start of the study was 7-13 kg. The animals were given food and water ad libitum.

The drug or control was administered by continuous intravenous infusion via indwelling catheters at the rates described above for 30 days. The total volume of fluid into the animals was 8.99 ml/kg/day for the 30 day period.

At the end of the 30 days the animals were sacrificed. Bone changes were observed on gross necropsy for animals receiving 250 and 80 ng/kg/minute of the $PGE_1$. For the animals receiving 250 ng/kg/minute the periosteum was rough, thickened, and appeared wet on the surface. On cross section the original cortical bone was observed to be surrounded by new bone approximately 3-5 mm thick. The bone marrow cavity also contained new bone in some areas. Microscopic changes indicative of active osteogenesis were evident in the ribs and vertebrae. A similar bone deposition was discovered in the long bones of the limbs of the dogs receiving 80 and 25 ng/kg/minute, however, the change in these animals was of a lesser degree.

EXAMPLE 2

Prostaglandin $E_2$ was administered orally in gelatin capsules to beagle dogs (4 per sex per group) at dosages of 1.0, 3.2, and 10.0 mg/kg/day in equally divided doses, for 90 days. A control group received vehicle (95% ethanol:triacetin).

Clinical signs (loose stools to diarrhea, vomiting, injected sclerae), generally associated with prostaglandin administration were observed during the dosing period. No skeletal abnormalities were observed. Preliminary evaluation of blood chemistries showed an increase in serum alkaline phosphatase with little or no change in serum calcium and phosphorus, with this increase most apparent in the high dose group.

Preliminary cortical (femur and rib) bone evaluation reveals the following: Grossly, all intact bones appeared normal at all dose levels. On cross-section and examination of "ground sections" the femurs of the high dose (10 mg/kg/day) group were increased in diameter (40%, 1.0 mm) by subperiosteal new bone encircling the original cortical bone. The new bone appeared compact and to closely resemble mature lamellar bone. Subperiosteal and in some areas, endosteal new bone, the percentage of active forming sites, and the accretion rate of bone were all increased in both femurs and ribs compared to matched controls. Microscopically subperiosteal new bone was observed in the low dosage (1.0 mg/kg/day). Compared to controls the number of remodeling foci and the percentage of active forming sites was increased in ribs at the low and medium dosages. In addition, the accretion rate of bone in both ribs of dogs of the medium and low dosages, and the femur of dogs of the medium dosage, was greater than that of matched controls.

FORMULA

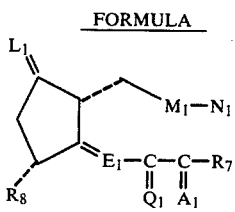

I

We claim:
1. A method for the treatment or prevention of non-growth related osteoporosis in an animal suffering from or susceptible to osteoporosis which comprises systemically administering to said animal an amount of a compound of the Formula I

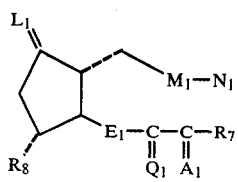

wherein $N_1$ is
(1) —$COOR_1$, wherein $R_1$ is
  (a) hydrogen,
  (b) $(C_1-C_{12})$alkyl
  (c) $(C_1-C_{10})$cycloalkyl,
  (d) $(C_6-C_{12})$aralkyl,
  (e) phenyl, optionally substituted with one, 2 or 3 chloro or $(C_1-C_3)$alkyl,
  (f) phenyl substituted in the para position by
    (i) —NH—CO—$R_{25}$,
    (ii) —CO—$R_{26}$,
    (iii) —O—CO—$R_{54}$, or
    (iv) —CH=N—NH—CO—$NH_2$ wherein $R_{25}$ is methyl, phenyl, acetamidophenyl, benzamidophenyl, or —$NH_2$; $R_{26}$ is methyl, phenyl, —$NH_2$, or methoxy; and $R_{54}$ is phenyl or acetamidophenyl; inclusive, or
  (g) a pharmacologically acceptable cation;
(2) —$CH_2OH$,
(3) —$COL_4$, wherein $L_4$ is
  (a) amino of the formula —$NR_{51}R_{52}$, wherein $R_{51}$ and $R_{52}$ are
    (i) hydrogen
    (ii) $(C_1-C_{12})$alkyl,
    (iii) $(C_3-C_{10})$cycloalkyl,
    (iv) $(C_7-C_{12})$aralkyl,
    (v) phenyl, optionally substituted with one, 2 or 3 chloro, $(C_1-C_3)$alkyl, hydroxy, carboxy, $(C_2-C_5)$alkoxycarbonyl, or nitro,
    (vi) $(C_2-C_5)$carboxyalkyl,
    (vii) $(C_2-C_5)$carbamoylalkyl,
    (viii) $(C_2-C_5)$cyanoalkyl,
    (ix) $(C_3-C_6)$acetylalkyl,
    (x) $(C_7-C_{11})$benzoalkyl, optionally substituted by one, 2 or 3 chloro, $(C_1-C_3)$alkyl, hydroxy, $(C_1-C_3)$alkoxy, carboxy, $(C_2-C_5)$alkoxycarbonyl, or nitro,
    (xi) pyridyl, optionally substituted by one, 2 or 3 chloro, $(C_1-C_3)$alkyl, or $(C_1-C_3)$alkoxy,
    (xii) $(C_6-C_9)$pyridylalkyl optionally substituted by one, 2 or 3 chloro, $(C_1-C_3)$alkyl,
    (xiii) $(C_1-C_4)$hydroxyalkyl,
    (xiv) $(C_1-C_4)$dihydroxyalkyl,
    (xv) $(C_1-C_4)$trihydroxyalkyl,
    with the further proviso that not more than one of $R_{51}$ and $R_{52}$ is other than hydrogen or alkyl,
  (b) cycloamino selected from the group consisting of pyrolidino, piperidino, morpholino, piperazino, hexamethyleneimino, pyrrolino, or 3,4-didehydropiperidinyl optionally substituted by one or 2 $(C_1-C_{12})$alkyl of one to 12 carbon atoms, inclusive,
  (c) carbonylamino of the formula —$NR_{53}COR_{51}$, wherein $R_{53}$ is hydrogen or $(C_1-C_4)$alkyl and $R_{51}$ is other than hydrogen, but otherwise as defined above,
  (d) sulfonylamino of the formula —$NR_{53}SO_2R_{51}$, wherein $R_{51}$ and $R_{53}$ are as defined in (c),
  (e) —$CH_2NL_2L_3$, wherein $L_2$ and $L_3$ are hydrogen or $(C_1-C_4)$alkyl, being the same or different, or the pharmacologically acceptable acid addition salts thereof when $N_1$ is —$CH_2NL_2L_3$,
  (f) —$CO_2R_1$,
  (g) —$CH_2OH$,
  (h) —$CONR_5R_6$,
  (i) —$CH_2$—$NR_5R_6$, or
  (j) —$CONHSO_2CH_3$;
wherein $M_1$ is cis or trans—CH=CH—$(CH_2)_m$—, —$(CH_2)_n$—, —$(CH_2)_{n-1}$—$CF_2$—, —CO—$(CH_2)_3$—$CH_2$—, trans—$(CH_2)_m$—CH=CH—; —CH=CH—$(CH_2)_{m-1}$— $CF_2$—, or —CO—$(CH_2)_3$—$CF_2$—;
wherein $L_1$ is α—OH:β—H, =$CH_2$, or oxo;
wherein $R_8$ is hydrogen, hydroxy, or methyl;
wherein $E_1$ is trans—CH=CH, —$CH_2$—$CH_2$—, or —C≡C—;
wherein $Q_1$ is α—OH:β—$R_2$, α-$R_2$:β—OH, or oxo;
wherein $A_1$ is α—H:β—$CH_3$, α—$CH_3$:β—H; α—H:-β—H, α—F:β—F or α—$CH_3$:β—$CH_3$;
wherein $R_7$ is:
  (1) —$(CH_2)_p$—$CH_3$,
  (2) cis—CH=CH—$CH_2$—$CH_3$,
  (3) —$(CH_2)_2$—C≡CH,
  (4) —$(CH_2)_3$—CH=$C(CH_3)_2$, or
  (5) —$C(R_3R_4)$—$(CH_2)_g$—$CH_2R_{14}$;
wherein $R_2$ is hydrogen or methyl;
wherein $R_3$ and $R_4$ are the same or different and are hydrogen or methyl;
wherein $R_5$ and $R_6$ are the same or different and are hydrogen, methyl, or ethyl;
wherein $R_{14}$ is hydrogen or $(C_1-C_4)$alkyl;
wherein g is an integer of from one to 4, inclusive;
wherein m is an integer of from 3 to 5, inclusive;
wherein n is an integer of from 5 to 7, inclusive; 5 or 7; and
wherein p is an integer from one to 6, inclusive or the pharmacologically acceptable salts thereof when $N_1$ is —$CONR_{53}SO_2R_{51}$; in an amount effective to treat or prevent said osteoporosis.

2. A method of claim 1 wherein $N_1$ is —$CO_2R_1$; $M_1$ is —CH=CH—$(CH_2)_m$— or —$(CH_2)_n$—; $L_1$ is oxo; $R_8$ is hydroxy; $Q_1$ is α—OH:β—$R_2$; and $A_1$ is α—H:β—H.

3. A method of claim 2 wherein $M_1$ is —CH=CH—$(CH_2)_m$—; $E_1$ is trans—CH=CH—; and $R_7$ is —$(CH_2)_p$—$CH_3$ or cis—CH=CH—$CH_2$—$CH_3$.

4. A method of claim 3 wherein the mode of administration is oral.

5. A method of claim 4 wherein the animal is a human.

6. A method of claim 5 wherein the compound is $PGE_2$.

7. A method of claim 1, wherein said compound of the formula I is selected from the group consisting of
PGE$_1$;
2-decarboxy-2-hydroxymethyl-PGE$_1$;
PGE$_2$;
15-keto-PGE$_2$;
16,16-dimethyl-PGE$_2$;
17S,20-dimethyl-6-oxo-PGE$_1$, methyl ester;
17S,20-dimethyl-trans-delta-2-PGE$_1$;
PGE$_2$, N-methanesulfonylamide;
9-deoxo-9-methylene-16,16-dimethyl-PGE$_2$;
(15S)-15-methyl-PGE$_2$;
(15R)-15-methyl-PGE$_2$;
11-deoxy-16,16-dimethyl-PGE$_2$;
11-deoxy-11$\alpha$-16,16-trimethyl-PGE$_2$;
6-oxo-11-deoxy-11$\alpha$,16,16-trimethyl-PGE$_2$;
6-oxo-PGE$_2$;
6-oxo-PGE$_1$;
2-decarboxy-2-hydroxymethyl-PGE$_1$;
11-deoxy-15-methyl-PGE$_1$;
PGE$_3$;
16,16-difluoro-PGE$_2$; and
20-isopropylidene-PGE$_1$.

* * * * *

UNITED STATES PATENT OFFICE
CERTIFICATE OF CORRECTION

Patent No. 4,621,100   Dated 4 November 1986

Inventor(s) John E. Lund

It is certified that error appears in the above-identified patent and that said Letters Patent are hereby corrected as shown below:

Column 6, lines 5-10 (Formula I): " 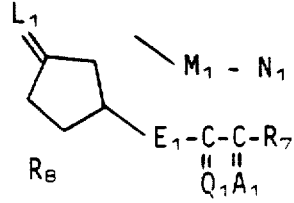 "

should read -- 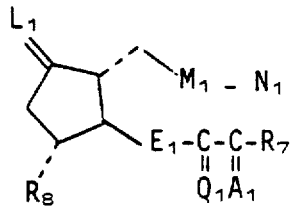 --.

Signed and Sealed this

Twentieth Day of October, 1987

Attest:

DONALD J. QUIGG

Attesting Officer   Commissioner of Patents and Trademarks